United States Patent
Wu et al.

(10) Patent No.: US 10,428,052 B2
(45) Date of Patent: Oct. 1, 2019

(54) PROCESS FOR PREPARING LIFITEGRAST AND INTERMEDIATES THEREOF

(71) Applicant: ScinoPharm Taiwan, Ltd., Tainan (TW)

(72) Inventors: Ming-Chih Wu, Tainan (TW); Tsung-Yu Hsiao, Tainan (TW)

(73) Assignee: ScinoPharm Taiwan, Ltd., Tainan (TW)

( * ) Notice: Subject to any disclaimer, the term of this patent is extended or adjusted under 35 U.S.C. 154(b) by 0 days.

(21) Appl. No.: 16/023,580

(22) Filed: Jun. 29, 2018

(65) Prior Publication Data

US 2019/0002445 A1    Jan. 3, 2019

Related U.S. Application Data

(60) Provisional application No. 62/527,868, filed on Jun. 30, 2017.

(51) Int. Cl.
*C07D 405/06* (2006.01)
*C07D 405/12* (2006.01)

(52) U.S. Cl.
CPC ......... *C07D 405/12* (2013.01); *C07D 405/06* (2013.01)

(58) Field of Classification Search
CPC .................................. C07D 405/06
USPC ........................................ 546/146
See application file for complete search history.

(56) References Cited

U.S. PATENT DOCUMENTS

| | | |
|---|---|---|
| 7,314,938 B2 * | 1/2008 | Shen ..................... C04B 35/632 546/146 |
| 8,080,562 B2 | 12/2011 | Burnier et al. |
| 8,378,105 B2 | 2/2013 | Burnier |
| 8,871,935 B2 | 10/2014 | Brunier et al. |
| 9,353,088 B2 | 5/2016 | Burnier et al. |
| 9,708,303 B2 | 7/2017 | Zeller et al. |
| 2003/0008848 A1 | 1/2003 | Fleck et al. |
| 2011/0124669 A1 | 5/2011 | Shen et al. |
| 2015/0336939 A1 | 11/2015 | Zeller et al. |
| 2016/0090361 A1 | 3/2016 | Tweedie et al. |

FOREIGN PATENT DOCUMENTS

CN    106995439 A    8/2017

OTHER PUBLICATIONS

International Search Report and Written Opinion dated Oct 11, 2018 corresponding to PCT/SG2018/050310 filed Jun. 26, 2018; 16 pages.

* cited by examiner

*Primary Examiner* — Deepak R Rao
(74) *Attorney, Agent, or Firm* — Mintz, Levin, Cohn, Ferris and Popeo, P.C.

(57) ABSTRACT

The present disclosure provides efficient, economical, and improved processes for synthesizing lifitegrast and intermediates thereof. The currently discloses processes provide a direct synthetic route, avoiding protection or deprotection steps. The currently disclosed process also provides processes for synthesizing lifitegrast using a reduced number of synthetic steps.

21 Claims, No Drawings

PROCESS FOR PREPARING LIFITEGRAST AND INTERMEDIATES THEREOF

CROSS-REFERENCES TO RELATED APPLICATIONS

This application claims the benefit of U.S. Provisional Patent Application No. 62/527,868, filed Jun. 30, 2017, which is incorporated herein in its entirety and for all purposes.

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

Lifitegrast (trade name Xiidra) is a drug for the treatment of keratoconjunctivitis sicca (dry eye syndrome). The chemical name of lifitegrast is (S)-2-(2-(benzofuran-6-carbonyl)-5,7-dichloro-1,2,3,4-tetrahydroisoquinoline-6-carboxamido)-3-(3-(methyl sulfonyl)phenyl) propanoic acid. The molecular formula of lifitegrast is $C_{29}H_{24}Cl_2N_2O_7S$ and its molecular weight is 615.5. Lifitegrast is a white to off-white powder which is soluble in water and a formula as shown below:

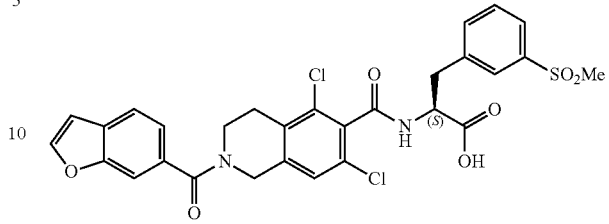

It was originally developed by Shire in 2013. The Drug Administration (FDA) approval for Xiidra (lifitegrast ophthalmic solution) 5%, a twice-daily eye drop indicated for the treatment of the signs and symptoms of dry eye disease in adult patients on July 2016.

U.S. Pat. No. 8,080,562B2 reveals two approaches for general lifitegrast synthesis. IM1 or IM3 is reacted with IM4 in the presence of HATU as a coupling reagent to provide IM5 or IM5a. In the subsequent hydrolysis step, IM5 or IM5a is treated with HCl in dioxane to provide IM6. Next, the in situ generated benzofuranoyl chloride (from IM7) was combined with IM6 to afford IM8 ($R_1$=Bn) or IM8a. Finally, lifitegrast is conducted by deprotection (i.e. removal of the Bn group by using hydrogenolysis). See Scheme 1 below.

Scheme 1: Preparation of Lifitergrast Disclosed in U.S. Pat. No. 8,080,562 B2

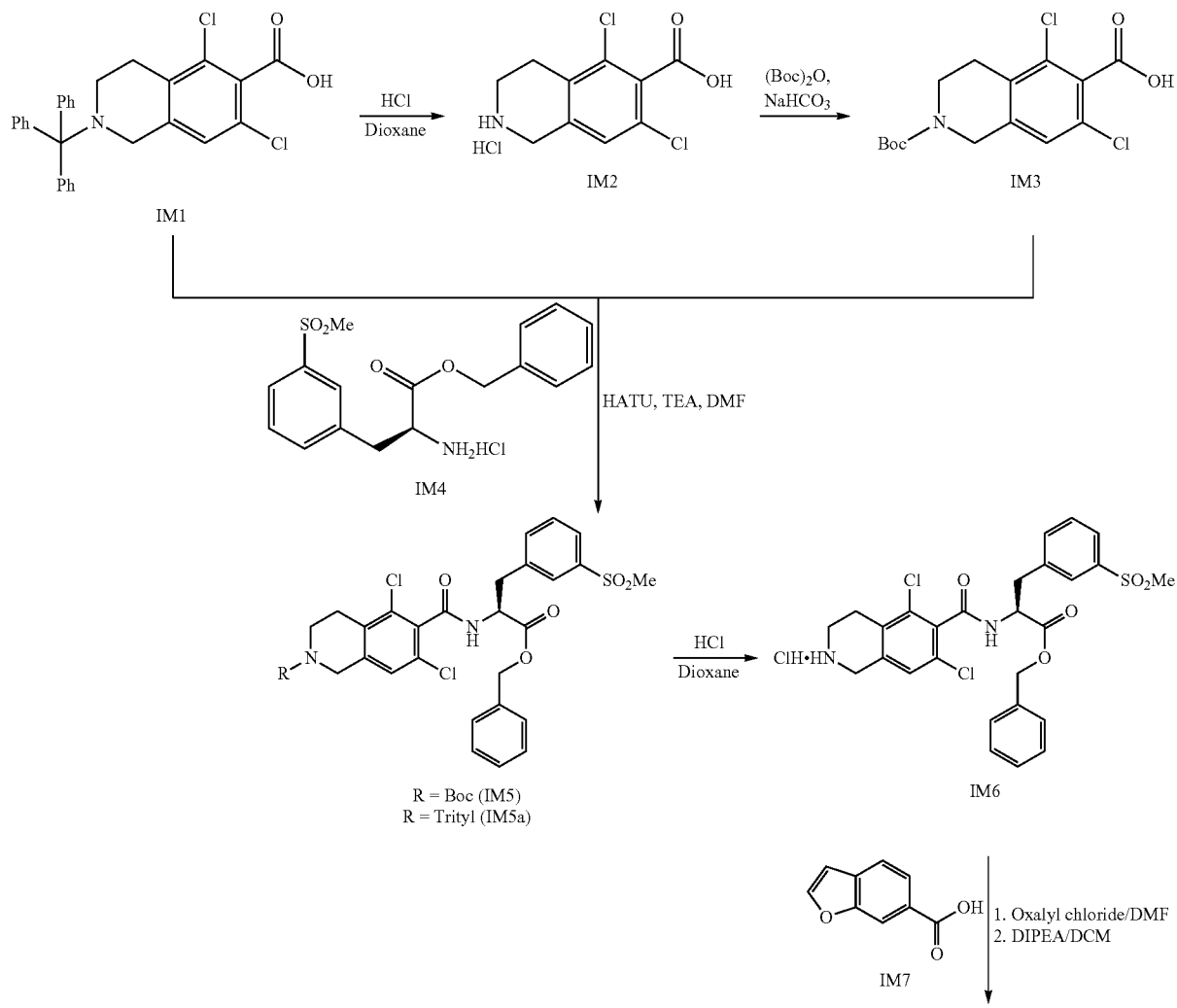

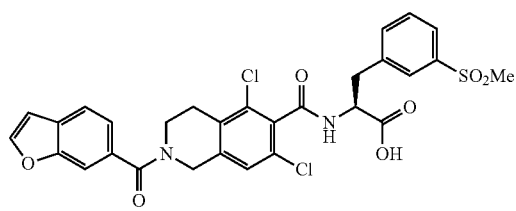

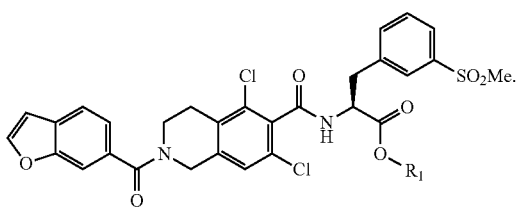

Lifitegrast

R₁ = Bn (IM8)
R₁ = (IM8a) is a carbon-containing moiety or a silyl-containing moiety U.S. Pat. No. 9,353,088B2 disclosed the hydrolysis of IM8 or IM8a by using sodium hydroxide as base to obtain lifitegrast. U.S. Pat. No. 8,378,105B2 disclosed the hydrolysis process by using acid (i.e. HCl) or base (i.e. NaOH) in presence of aprotic solvent (i.e. dioxane). U.S. Patent Application Publication No. 20150336939A1 also disclosed that the reaction mixture is biphasic during the hydrolysis. In addition, U.S. Pat. No. 8,871,935B2 disclosed the hydrogenolysis of an ester (IM8) with a palladium catalyst in presence of MeOH/THF (5:1) as solvent. Given this transfer hydrogenolysis process, the lifitegrast with high optical purity (98.5%) of (S)-enantiomer was obtained, as compared to 79%/o to 94.5% (S)-enantiomer optical purity obtained by hydrolysis of the corresponding methyl ester. See Scheme 2 below:

Scheme 2: Preparation of Lifitergrast Disclosed in U.S. Pat. No. 9,353,088 B2, U.S. Pat. No. 8,378,105 B2, US20150336939 A1 and U.S. Pat. No. 8,871,935 B2

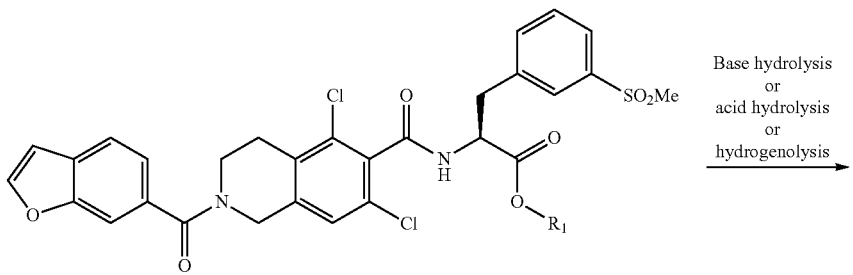

R₁ = Bn (IM8)
R₁ = (IM8a) is a carbon-containing moiety or a silyl-containing moiety

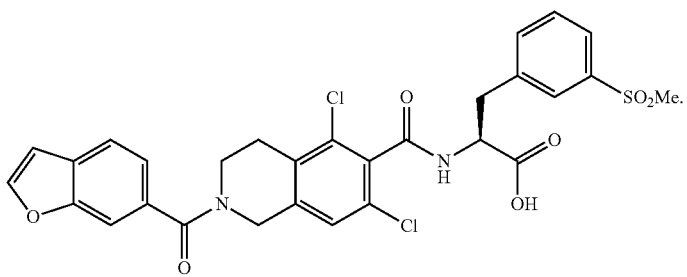

Lifitegrast

Despite the above described processes, there remains a need for the development of more efficient and improved processes for the preparation of lifitegrast. The present disclosure addresses this need and provides related advantages as well.

SUMMARY OF THE INVENTION

In one aspect, the present invention provides a process for preparing lifitegrast (Formula I):

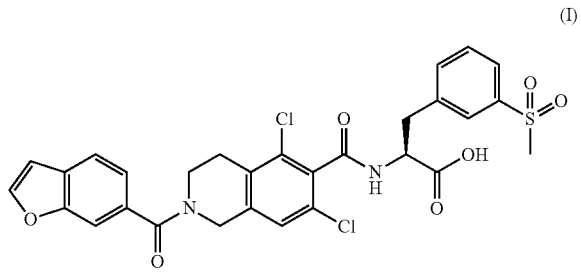 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

(I)

or a pharmaceutically acceptable salt thereof; the process comprising:

contacting the compound of Formula IV

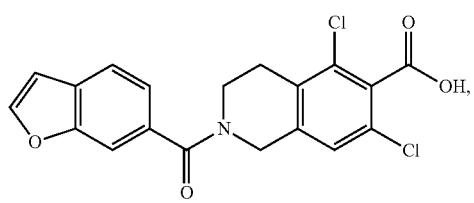

(IV)

with an activating reagent in an activating solvent to provide an activated intermediate of Formula IVa

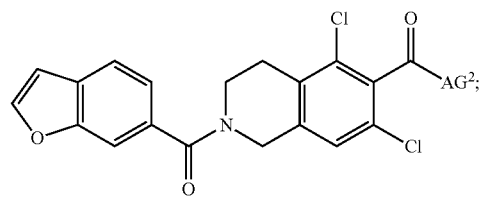

(IVa)

and contacting the activated intermediate of Formula IVa with a compound of Formula V or V'

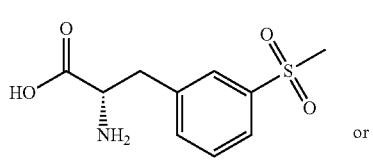

(V)

or

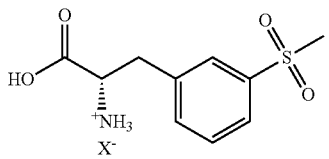

(V')

in a coupling solvent to provide a compound of Formula I;

wherein AG² is Cl or an activated hydroxyl moiety and X⁻ is Cl⁻, Br⁻, I⁻, or CF₃C(O)O⁻.

In another aspect, the present application provides a process for preparing lifitegrast (Formula I):

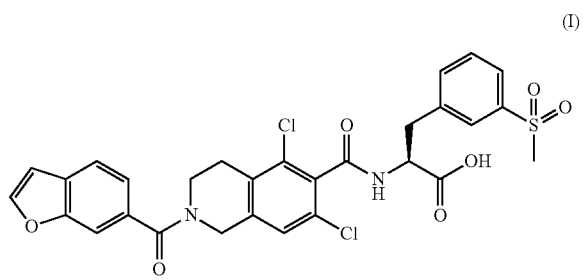 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

(I)

or a pharmaceutically acceptable salt thereof; the process comprising:

a) contacting the compound of Formula II

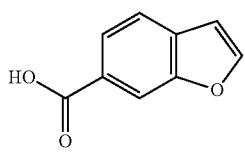

(II)

with a first activating reagent in a first activating solvent to provide an activated intermediate of Formula IIa

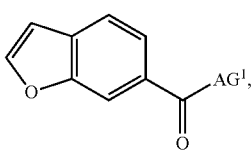

(IIa)

and contacting the activated intermediate of Formula IIa with a compound of Formula III or III'

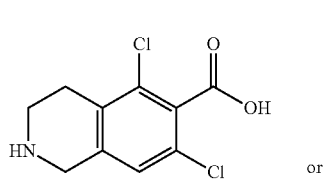

(III)

or

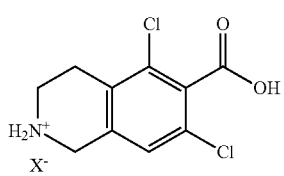

in a first coupling solvent to provide a compound of Formula IV

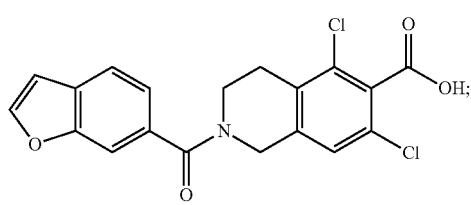

and b) contacting the compound of Formula IV with a second activating reagent in a second activating solvent to provide an activated intermediate of Formula IVa

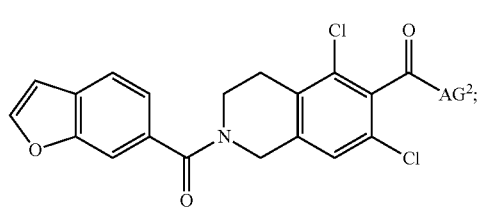

and contacting the activated intermediate of Formula IVa with a compound of Formula V or V'

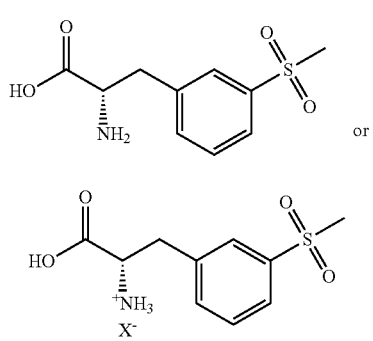

in a second coupling solvent to provide a compound of Formula I;

wherein $AG^1$ and $AG^2$ are each independently Cl or an activated hydroxyl moiety and $X^-$ is $Cl^-$, $Br^-$, $I^-$, or $CF_3C(O)O^-$.

BRIEF DESCRIPTION OF THE DRAWINGS

Not applicable

DETAILED DESCRIPTION

I. General

The present invention provides improved processes for the preparation of lifitegrast and intermediates thereof. Specifically, the presently disclosed processes do not require any protection or deprotection steps and the processes reduce the total number of synthetic steps required to reach the desired product. The removal of synthetic steps saves a significant amount of time and resources by removing previously required processing and handling steps.

II. Definitions

As used herein, the term "forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "alkyl" by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_4$ means one to four carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, and the like.

As used herein, the term "alkyl-alcohol" refers to a straight or branched chain hydrocarbon radical with a hydroxyl substituent replacing a hydrogen. Alkyl-alcohol moieties, can have alkyl lengths as defined for "alkyl" above. Examples of alkyl-alcohols include methanol, ethanol, 1-propanol, 2-propanol, 1-butanol, 2-butanol, tert-butyl alcohol, and the like.

III. Description of the Embodiments

In one aspect, the present application provides a process for preparing lifitegrast (Formula I):

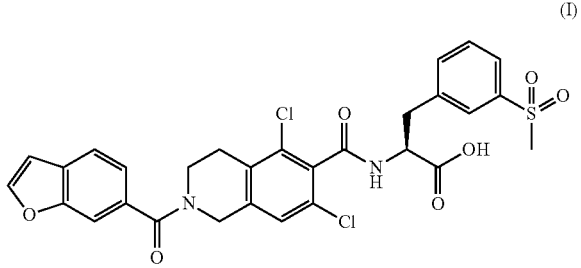

or a pharmaceutically acceptable salt thereof; the process comprising:

a) contacting the compound of Formula II

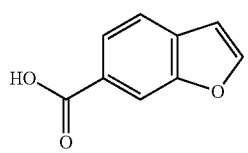

with a first activating reagent in a first activating solvent to provide an activated intermediate of Formula IIa

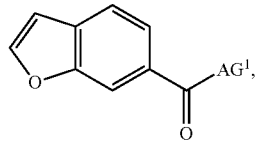

and contacting the activated intermediate of Formula IIa with a compound of Formula III or III'

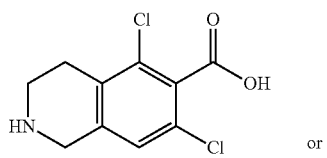

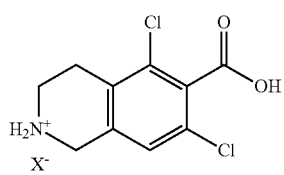

in a first coupling solvent to provide a compound of Formula IV

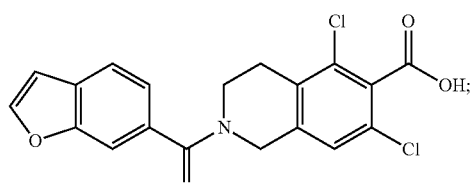

and b) contacting the compound of Formula IV with a second activating reagent in a second activating solvent to provide an activated intermediate of Formula IVa

and contacting the activated intermediate of Formula IVa with a compound of Formula V or V'

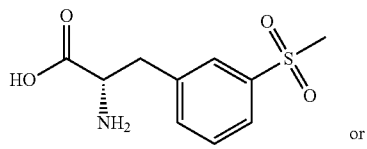

or

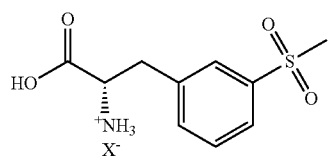

in a second coupling solvent to provide a compound of Formula I;

wherein $AG^1$ and $AG^2$ are each independently Cl or an activated hydroxyl moiety and $X^-$ is $Cl^-$, $Br^-$, $I^-$, or $CF_3C(O)O^-$.

In some embodiments, the first activating solvent and the first coupling solvent are each a first solvent and the second activating solvent and the second coupling solvent are each a second solvent.

In some embodiments, the process includes forming a first reaction mixture including the compound of Formula II, the first activating reagent, and the first solvent to provide the compound of Formula IV; and forming a second reaction mixture including the compound of Formula IV, the second activating reagent, and the second solvent to provide the compound of Formula I.

In some embodiments, the present application provides a process for preparing lifitegrast (Formula I):

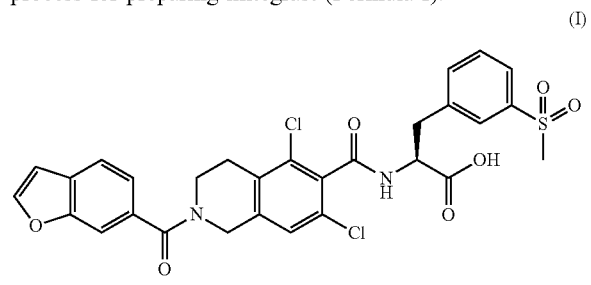
(I)

or a pharmaceutically acceptable salt thereof; the process comprising:

a) forming a first reaction mixture by contacting the compound of Formula II

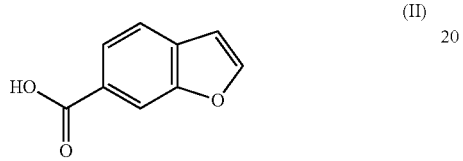
(II)

with a first activating reagent to provide an activated intermediate of Formula IIa

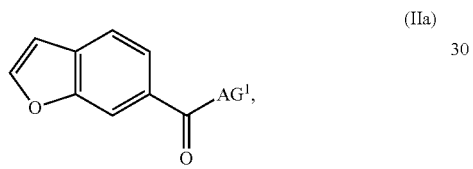
(IIa)

and
contacting the activated intermediate of Formula IIa with a compound of Formula III or III'

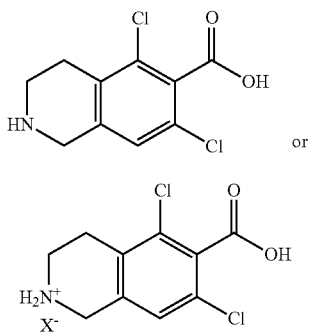
(III)

or (III')

to provide a compound of Formula IV

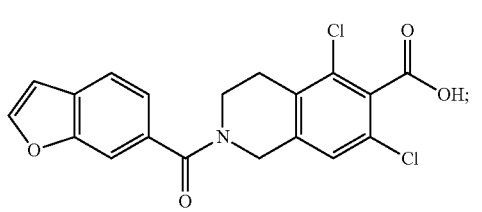
(IV)

and b) forming a second reaction mixture by contacting the compound of Formula IV with a second activating reagent to provide an activated intermediate of Formula IVa

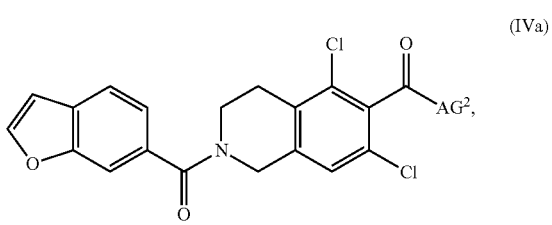
(IVa)

and
contacting the activated intermediate of Formula IVa with a compound of Formula V or V'

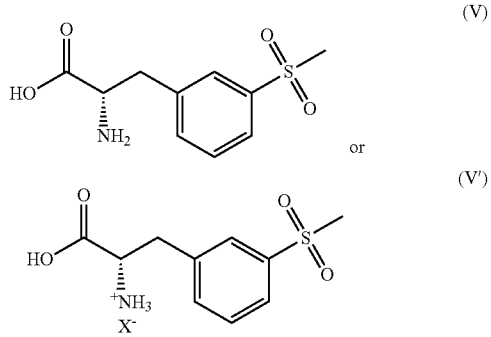
(V)

or (V')

to provide a compound of Formula I;
wherein $AG^1$ and $AG^2$ are each independently Cl or an activated hydroxyl moiety and $X^-$ is $Cl^-$, $Br^-$, $I^-$, or $CF_3C(O)O^-$.

In some embodiments, the first reaction mixture comprises a first solvent and the second reaction mixture comprises a second solvent.

A variety of solvents are suitable for the first solvent and/or the second solvent. In some embodiments, the first solvent and/or the second solvent is selected from the group consisting of $C_{1-4}$ alkyl-alcohol, dioxane, N-methyl-2-pyrrolidone (NMP), dimethylacetamide (DMAc), N,N-dimethylmethanamide (DMF), ethyl acetate, acetonitrile, tetrahydrofuran (THF), dimethyl sulfoxide (DMSO), dichloromethane (DCM), toluene, water, and mixtures thereof. In some embodiments, the first and the second solvent are the same. In some embodiments, the first and the second solvent are both THF. In some embodiments, the first solvent is selected from DMF, THF, or mixtures thereof. In some embodiments, the first solvent is selected from DMF, toluene, or a combination thereof. In some embodiments, the second solvent is selected from DCM, acetonitrile, and mixtures thereof.

In some embodiments, the first activating solvent is used in the conversion of the compound of Formula II to the Compound of Formula IIa, and the first coupling solvent is used when contacting the compound of Formula IIa with the Compound of Formula III or III' to form the compound of Formula IV. In some embodiments, the first activating solvent and the first coupling solvent are each independently selected from $C_{1-4}$ alkyl-alcohol, dioxane, N-methyl-2-pyrrolidone (NMP), dimethylacetamide (DMAc), N,N-dimethylmethanamide (DMF), ethyl acetate, acetonitrile, tetrahydrofuran (THF), dimethyl sulfoxide (DMSO), dichloromethane, toluene, water, and mixtures thereof. In some embodiments, the first activating solvent and the first coupling solvent are the same. In some embodiments, the first activating solvent is selected from DMF/THF, DMF/DCM, and DMF/toluene. In some embodiments, the first coupling solvent is THF or toluene. In some embodiments, the first coupling solvent is THF. In some embodiments, the first coupling solvent is toluene. In some embodiments, the first activating solvent is DMF/THF and the first coupling solvent is THF. In some embodiments, the first activating solvent is DMF/toluene and the first coupling solvent is toluene.

In some embodiments, the second activating solvent is used in the conversion of the compound of Formula IV to the Compound of Formula IVa, and the second coupling solvent is used when contacting the compound of Formula IVa with the Compound of Formula V or V' to form the compound of Formula I. In some embodiments, the second activating solvent and the second coupling solvent are each independently selected from $C_{1-4}$ alkyl-alcohol, dioxane, N-methyl-2-pyrrolidone (NMP), dimethylacetamide (DMAc), N,N-dimethylmethanamide (DMF), ethyl acetate, acetonitrile, tetrahydrofuran (THF), dimethyl sulfoxide (DMSO), dichloromethane, toluene, water, and mixtures thereof. In some embodiments, the second activating solvent and the second coupling solvent are the same. In some embodiments, the second activating solvent is selected from DMF, DCM, toluene, and mixtures thereof. In some embodiments, the second activating solvent is DMF/toluene. In some embodiments, the second activating solvent is THF. In some embodiments, the second coupling solvent is acetonitrile, or THF. In some embodiments, the second coupling solvent is acetonitrile. In some embodiments, the second coupling solvent is THF. In some embodiments, the second activating solvent and the second coupling solvent are both THF.

In some embodiments, the present application provides a process for preparing lifitegrast (Formula I):

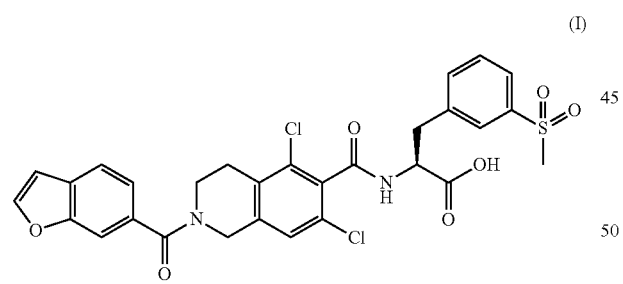

(I)

or a pharmaceutically acceptable salt thereof; the process comprising:
a) forming a first activating reaction mixture by contacting the compound of Formula II

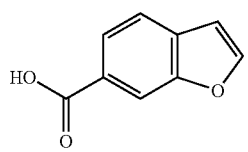

(II)

with a first activating reagent in a first activating solvent to provide an activated intermediate of Formula IIa

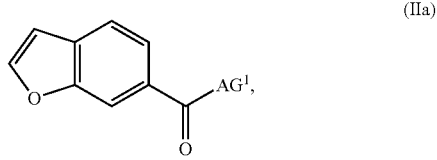

(IIa)

and
forming a first coupling reaction mixture by contacting the activated intermediate of Formula IIa with a compound of Formula III or III'

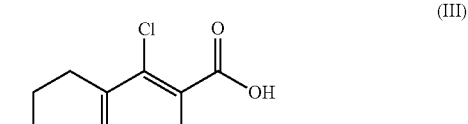

(III)

or

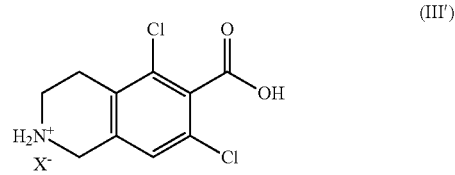

(III')

in a first coupling solvent to provide a compound of Formula IV

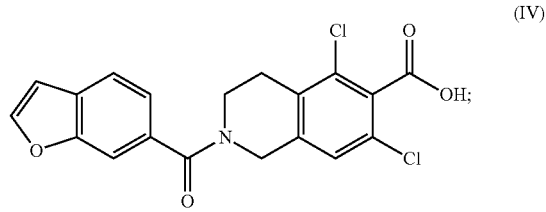

(IV)

and
b) forming a second activating reaction mixture by contacting the compound of Formula IV with a second activating reagent in a second activating solvent to provide an activated intermediate of Formula IVa

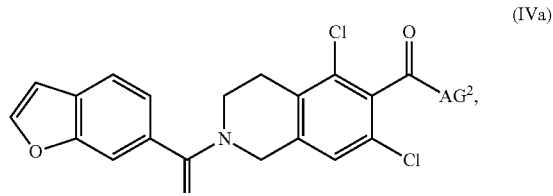

(IVa)

and
forming a second coupling reaction mixture by contacting the activated intermediate of Formula IVa with a compound of Formula V or V'

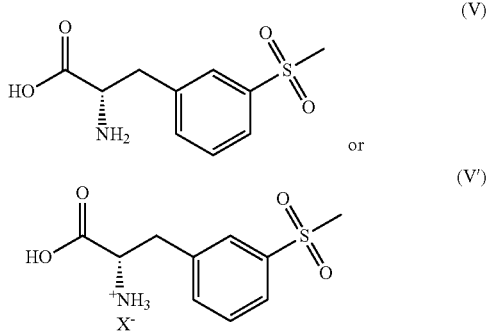

in a second coupling solvent to provide a compound of Formula I;

wherein AG¹ and AG² are each independently Cl⁻ or an activated hydroxyl moiety and X⁻ is Cl⁻, Br⁻, I⁻, or CF₃C(O)O⁻.

The first activating solvent, the first coupling solvent, the second activating solvent, and the second coupling solvent are as defined and described herein.

In some embodiments, the conversion of step a) and/or step b) further comprises a non-nucleophilic base. In some embodiments, the non-nucleophilic base is selected from the group consisting of triethylamine, N,N-diisopropylethylamine (DIPEA), and N-methylmorpholine. In some embodiments, the non-nucleophilic base is N,N-diisopropylethylamine (DIPEA). The non-nucleophilic base can be added during the activating or coupling portions of steps a) and/or b).

In some embodiments, the first activating reagent is a first chlorinating reagent. In some embodiments, the first chlorinating reagent is selected from the group consisting of (COCl)₂ (oxalyl chloride), SOCl₂ (thionyl chloride), POCl₃ (Phosphoryl chloride), and PCl₅ (phosphorus pentachloride). In some embodiments, the first chlorinating reagent is (COCl)₂ (oxalyl chloride). In some embodiments, the first chlorinating reagent is (SOCl)₂ (thionyl chloride).

In some embodiments, the second activating reagent is a second chlorinating reagent. In some embodiments, the second chlorinating reagent is selected from the group consisting of (COCl)₂ (oxalyl chloride), SOCl₂ (thionyl chloride), POCl₃ (Phosphoryl chloride), and PCl₅ (phosphorus pentachloride). In some embodiments, the second chlorinating reagent is (COCl)₂ (oxalyl chloride). In some embodiments, the second chlorinating reagent is (SOCl)₂ (thionyl chloride).

In some embodiments, the first chlorinating reagent and the second chlorinating reagent are the same. In some embodiments, the first chlorinating reagent and the second chlorinating reagent are different.

In some embodiments, the first chlorinating reagent and/or second chlorinating reagent is (COCl)₂ (oxalyl chloride). In some embodiments, the first chlorinating reagent and/or second chlorinating reagent is (SOCl)₂ (thionyl chloride). In some embodiments, the first chlorinating reagent and second chlorinating reagent are both (COCl)₂ (oxalyl chloride). In some embodiments, the first chlorinating reagent and second chlorinating reagent are both (SOCl)₂ (thionyl chloride). In some embodiments, the first chlorinating reagent is (COCl)₂ (oxalyl chloride) and second chlorinating reagent is (SOCl)₂ (thionyl chloride). In some embodiments, the first chlorinating reagent is (SOCl)₂ (thionyl chloride) and second chlorinating reagent is (COCl)₂ (oxalyl chloride).

In some embodiments, the first activating reagent is selected from the group consisting of dicyclohexylcarbodiimide (DCC), diisopropylcarbodiimide (DIC), 1-ethyl-3-(3-dimethylaminopropyl)carbodiimide (EDCI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), hydroxybenzotriazole (HOBt), 1-hydroxy-7-azabenzotriazole (HOAt), and mixtures thereof. In some embodiments, the first activating reagent is O-(7-azabenzotriazol-1-yl)-N,N,N',N'-tetramethyluronium hexafluorophosphate (HATU). In some embodiments, the first activating reagent is 1-hydroxy-7-azabenzotriazole (HOAt).

In some embodiments, the second activating reagent is selected from the group consisting of dicyclohexylcarbodiimide (DCC), diisopropylcarbodiimide (DIC), 1-ethyl-3-(3-dimethylaminopropyl)carbodiimide (EDCI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), hydroxybenzotriazole (HOBt), 1-hydroxy-7-azabenzotriazole (HOAt), and mixtures thereof. In some embodiments, the second activating reagent is O-(7-azabenzotriazol-1-yl)-N,N,N',N'-tetramethyluronium hexafluorophosphate (HATU). In some embodiments, the first activating reagent is 1-hydroxy-7-azabenzotriazole (HOAt).

In some embodiments, the first activating reagent and the second activating reagent are the same. In some embodiments, the first activating reagent and the second activating reagent are different.

AG¹ is an activating group, and its identity is dependent on the activating reagent used. For example, when the activating reagent is a chlorinating reagent, the compound of Formula IIa is the compound of Formula IIb

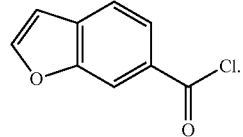

As an additional example, when the activating reagent is HOAt, the compound of Formula IVa is the compound of Formula IIc

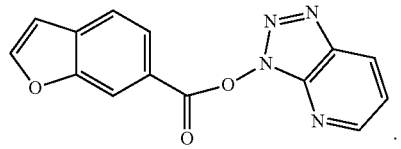

Any of the activating reagents for step a) described above may be used. Accordingly in some embodiments, AG¹ is Cl or an activated hydroxyl moiety. In some embodiments, the activated hydroxyl moiety is the reaction product of a carboxylic acid with dicyclohexylcarbodiimide (DCC), diisopropylcarbodiimide (DIC), 1-ethyl-3-(3-dimethylaminopropyl)carbodiimide (EDCI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), hydroxybenzotriazole (HOBt), 1-hydroxy-7-azabenzotriazole (HOAt), or mixtures thereof.

The compound of formula III can be in a salt form. In some embodiments, the salt form of formula III is a compound of formula III'

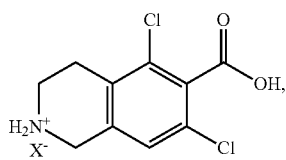

(III')

wherein X⁻ is Cl⁻, Br⁻, I⁻, or CF₃C(O)O⁻. In some embodiments, X⁻ is Cl⁻ or CF₃C(O)O⁻. In some embodiments, X⁻ is Cl⁻. In some selected embodiments, X⁻ is CF₃C(O)O⁻. In some embodiments, the compound of formula III' is a compound of formula III'a:

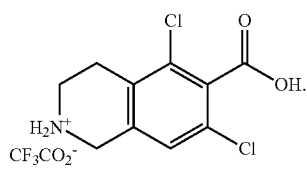

(III'a)

It is understood that the intermediate of Formula IIa can be isolated and stored under appropriate conditions. Appropriate storage conditions of chlorinated carboxylic acid groups are well known to a person of skill in the art and include removing the solvent and storing under nitrogen. It is further understood that the intermediate of Formula IIa may be directly reacted with Formula III or III' either after removal of some or all of the solvent from the activating step or without the removal of the solvent from the activating step. In some embodiments, the intermediate of Formula IIa is directly reacted with the compound of Formula III or III' without removal of any the first solvent or the first activating solvent. In some embodiments, the intermediate of Formula IIa is directly reacted with the compound of Formula III or III' after removal of some or all of the first activating solvent from the activating step.

Many temperatures are suitable for the first activating and first coupling conversion of step a). In some embodiments, the first activating and/or first coupling conversion of step a) are performed at about room temperature. In some embodiments the first activating and/or first coupling conversion of step a) are performed at a temperature of from about 20 to 30° C. In some embodiments, the temperature of the first activating conversion is from about 20-30° C. when preparing the reaction mixture, and after each reagent is included the reaction is heated to about 45-55° C. In some embodiments, the temperature of the first coupling conversion is lowered when the compound of Formula IIa and the compound of Formula III or III' are contacted. In some embodiments the lowered temperature is from about 0 to 15° C. or from about 0 to 10° C. After addition, the temperature is gradually returned to the previously described temperatures.

AG² is an activating group, and its identity is dependent on the activating reagent used. Any of the activating reagents for step a) described above may be used. For example, when the activating reagent is a chlorinating reagent, the compound of Formula IVa is the compound of Formula IVb

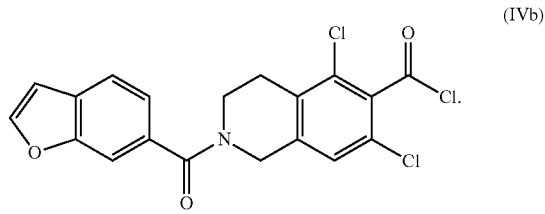 [SMILES: O=C(Cl)c1c(Cl)cc2c(c1Cl)CCN(C(=O)c1ccc3ccoc3c1)C2]

(IVb)

As an additional example, when the activating reagent is HOAt, the compound of Formula IVa is the compound of Formula IVc

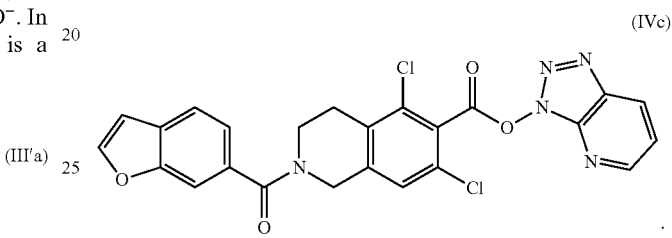

(IVc)

Any of the activating reagents for step a) described above may be used. Accordingly in some embodiments, AG² is Cl or an activated hydroxyl moiety. In some embodiments, the activated hydroxyl moiety is the reaction product of a carboxylic acid with dicyclohexylcarbodiimide (DCC), diisopropylcarbodiimide (DIC), 1-ethyl-3-(3-dimethylaminopropyl)carbodiimide (EDCI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), hydroxybenzotriazole (HOBt), 1-hydroxy-7-azabenzotriazole (HOAt), or mixtures thereof.

The compound of formula V can be in a salt form. In some embodiments, the salt form of formula V is a compound of formula V'

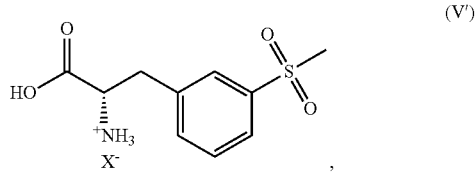

(V')

wherein X⁻ is Cl⁻, Br⁻, I⁻, or CF₃C(O)O⁻. In some embodiments, X⁻ is Cl⁻ or CF₃C(O)O⁻. In some embodiments, X⁻ is Cl⁻. In some selected embodiments, X⁻ is CF₃C(O)O⁻.

It is understood that the intermediate of Formula IVa can be isolated and stored under appropriate conditions. Appropriate storage conditions of chlorinated carboxylic acid groups are well known to a person of skill in the art and include removing the solvent and storing under nitrogen. It is further understood that the intermediate of Formula IVa may be directly reacted with Formula V or V' either after removal of some or all of the solvent from the second activating step or without the removal of the solvent from the second activating step. In some embodiments, the intermediate of Formula IVa is directly reacted with the compound of Formula V or V' without removal of any the second solvent or the second activating solvent. In some embodiments, the intermediate of Formula IVa is directly reacted with the compound of Formula V or V' after removal of some or all of the second activating solvent from the second activating step.

Many temperatures are suitable for the second activating and second coupling conversion of step b). In some embodiments, the second activating and/or second coupling conversion of step b) are performed at about room temperature. In some embodiments the second activating and/or second coupling conversion of step b) are performed at a temperature of from about 20 to 50° C. In some embodiments the second activating and/or second coupling conversion of step b) are performed at a temperature of from about 20 to 30° C. In some embodiments, the temperature of the second activating and/or second coupling conversion of step b) is performed at a temperature of from about 40-50° C. The second coupling conversion may be heated after the compound of Formula IVa and the compound of Formula V or V' are contacted. In some embodiments, the heated temperature is about 40° C. After a sufficient amount of time, the temperature is gradually returned to the previously described temperatures. A sufficient amount of time includes 30 minutes, 1 hours, 1.5 hours, 2 hours, 3 hours or more. In some embodiments a sufficient amount of time is 3 hours.

In another aspect, the present invention provides a process for preparing lifitegrast (Formula I):

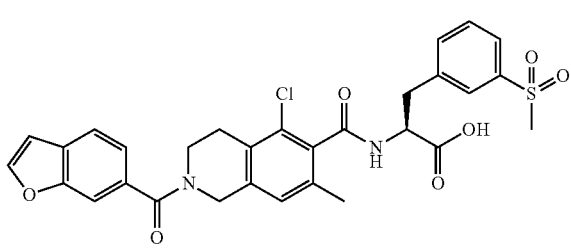

(I)

or a pharmaceutically acceptable salt thereof; the process comprising:
contacting the compound of Formula IV

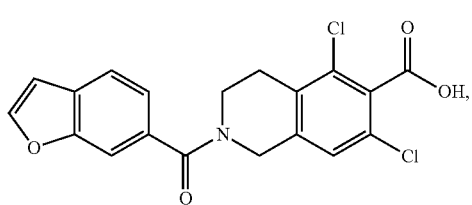

(IV)

with an activating reagent in an activating solvent to provide an activated intermediate of Formula IVa

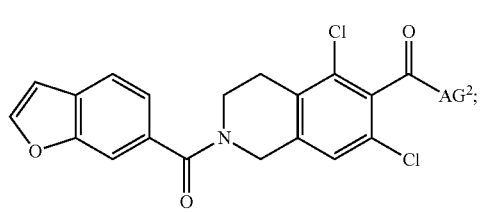

(IVa)

and
contacting the activated intermediate of Formula IVa with a compound of Formula V or

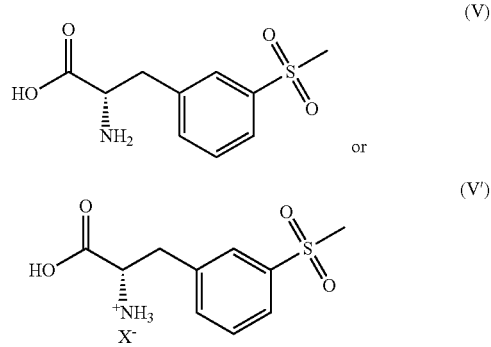

in a coupling solvent to provide a compound of Formula I;

wherein $AG^2$ is Cl or an activated hydroxyl moiety and $X^-$ is $Cl^-$, $Br^-$, $I^-$, or $CF_3C(O)O^-$.

In some embodiments, the activating solvent and the coupling solvent are each a solvent. The solvent can be any of the second solvents for step b) described above.

In some embodiments, the process includes forming a reaction mixture including the compound of Formula IV, the activating reagent, and the solvent to provide the compound of Formula I.

In some embodiments, the present invention provides a process for preparing lifitegrast (Formula I):

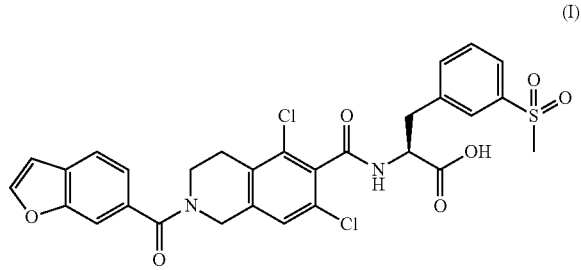 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

(I)

or a pharmaceutically acceptable salt thereof; the process comprising:
forming a reaction mixture by contacting the compound of Formula IV

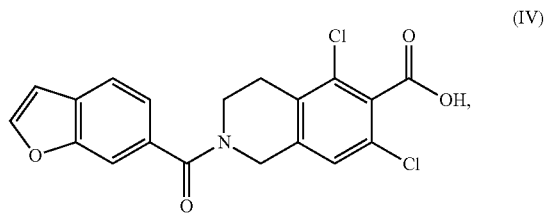 [SMILES: O=C(O)c1c(Cl)cc2c(c1Cl)CCN(C(=O)c1ccc3ccoc3c1)C2]

(IV)

with an activating reagent to provide an activated intermediate of Formula IVa

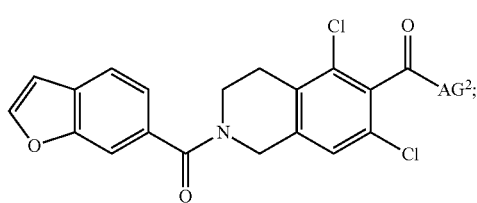
(IVa)

and contacting the activated intermediate of Formula IVa with a compound of Formula V or V'

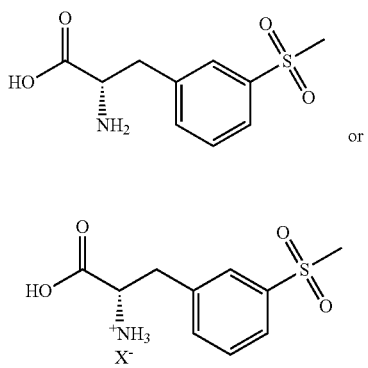
(V)

or (V')

to provide a compound of Formula I;
wherein $AG^2$ is Cl or an activated hydroxyl moiety and $X^-$ is $Cl^-$, $Br^-$, $I^-$, or $CF_3C(O)O^-$.

In some embodiments, the reaction mixture comprises a solvent. The solvent can be any of the second solvents for step b) described above.

In some embodiments, the activating solvent is used in the conversion of the compound of Formula IV to the Compound of Formula IVa, and the coupling solvent is used when contacting the compound of Formula IVa with the Compound of Formula V or V' to form the compound of Formula I.

In some embodiments, the present invention provides a process for preparing lifitegrast (Formula I):

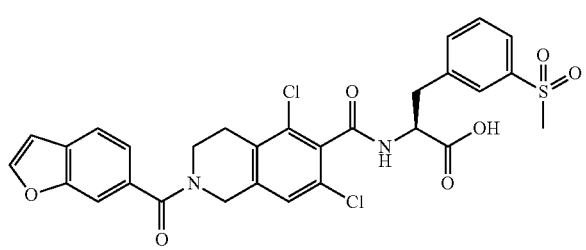
(I)

or a pharmaceutically acceptable salt thereof; the process comprising:

forming an activating reaction mixture by contacting the compound of Formula IV

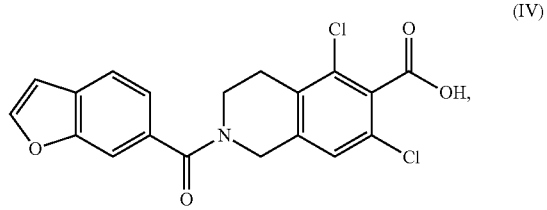 [SMILES: O=C(O)c1c(Cl)cc2c(c1Cl)CCN(C(=O)c1ccc3ccoc3c1)C2]
(IV)

with an activating reagent in an activating solvent to provide an activated intermediate of Formula IVa

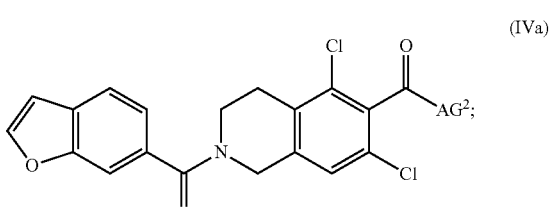
(IVa)

and forming a coupling reaction mixture by contacting the activated intermediate of Formula IVa with a compound of Formula V or V'

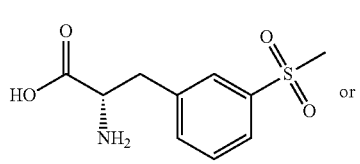
(V)

or

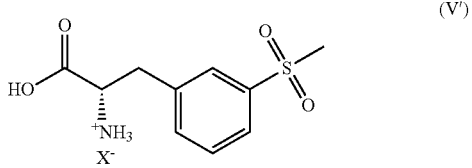
(V')

in a coupling solvent to provide a compound of Formula I;
wherein $AG^2$ is Cl or an activated hydroxyl moiety and $X^-$ is $Cl^-$, $Br^-$, $I^-$, or $CF_3C(O)O^-$.

The activating solvent can be any of the second activating solvents for step b) described above. The coupling solvent can be any of the second coupling solvents for step b) described above.

Suitable conditions for the above described process are those for step b) described above.

IV. EXAMPLES

The following examples are provided to further illustrate, but not to limit this invention.

Example 1: Preparation of the Compound of Formula IV

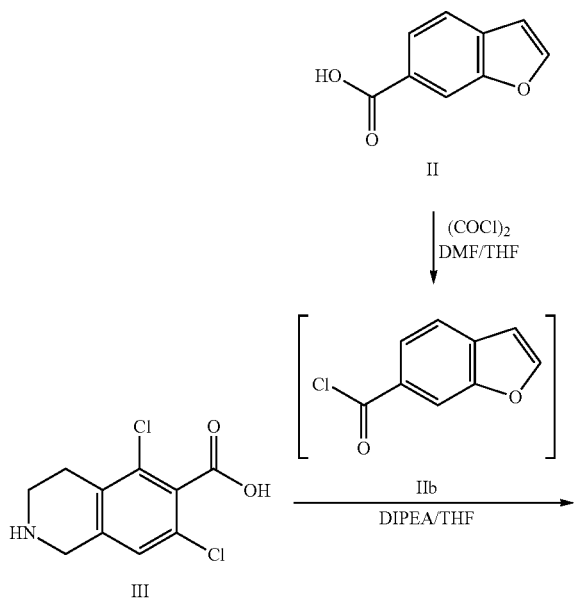

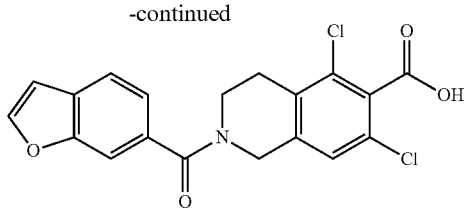

Benzofuran carboxylic acid (II) (1.0 g, 6.17 mmol, 1.0 equiv), DMF (0.01 eq) and THF (10 mL, 10 vol) is charged to a two-neck round bottom flask under nitrogen atmosphere. Oxalyl chloride (1.1 mL, 13.34 mmol, 2.0 equiv) is slowly added while keeping the temperature between 20 to 30° C. The resulting solution was stirred at 20-30° C. for over 2 hr. When the reaction was complete as determined by TLC analysis, the solvent was removed under reduced pressure and the acid chloride of compound of Formula II (Formula IIb) was stored under nitrogen.

Compound of Formula III (1.66 g, 6.74 mmol, 1 equiv) and THF (10 mL, 10 vol) were added to a two-neck round bottom flask equipped with a thermal couple and a magnetic stirrer. The mixture was added diisopropylamine (DIPEA) (1.6 mL, 9.2 mmol, 1.5 equiv) at NMT 30° C. The reaction mixture is cooled to 0 to 10° C. and a solution of compound of Formula IIb in THF (10 mL, 10 vol) was slowly added while keeping the temperature between 0 to 10° C. The reaction mixture was gradually warmed to 20-30° C. and until the reaction was complete. When the reaction was complete as determined by TLC analysis, the reaction mixture was added 2-propanol (IPA) (10 mL, 10 vol) and 1N HCl (5 mL, 5 mL). After the reaction mixtures stirred for NLT 2 hr at 20-30° C. The solid was filtered and the wet cake was washed with 1N HCl/IPA (15 mL, 2/1, 15 vol). The wet cake was dried below 60° C. under vacuum and nitrogen to afford compound of Formula IV (2.2 g, 91%).

Example 2: Preparation of Lifitegrast

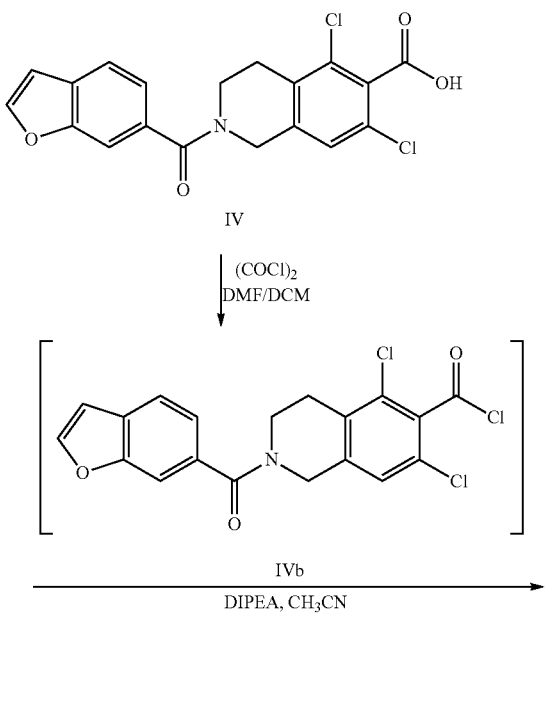

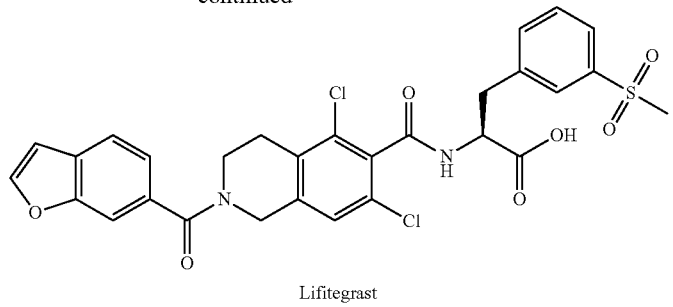

Lifitegrast

The compound of Formula IV (100 mg, 0.26 mmol, 1.0 equiv), DMF (0.01 eq) and DCM (0.5 mL, 5 vol) is charged to a two-neck round bottom flask under nitrogen atmosphere. Oxalyl chloride (45 µL, 0.52 mmol, 2.0 equiv) is slowly added while keeping the temperature between 20 to 30° C. The resulting solution was stirred at 20-30° C. for over 2 hr. When the reaction was complete as determined by TLC analysis, the solvent was removed under reduced pressure and the acid chloride of the compound of Formula IV (Formula IVb) was stored under nitrogen.

The compound of Formula V (75 mg, 0.31 mmol, 1.2 equiv), DIPEA (90 µL, 0.5 mmol, 2.0 equiv) and CH₃CN (1 mL, 13 vol) were added into a two-necked round bottom flask equipped with a magnetic stirrer and a thermometer under nitrogen at NMT 30° C. The reaction mixture was slowly added of a solution containing the compound of Formula IVb in DCM (1 mL, 13 vol) whilst maintaining the temperature at NMT 10° C. The resulting solution was warmed to 20-30° C. and stirred at 20-30° C. When the reaction was complete as determined by TLC analysis, the reaction was added water (3.8 mL, 50 vol). The solid was filtered and the wet cake was washed with water (140 µL, 2 vol). The wet cake was dried below 60° C. under vacuum and nitrogen to afford lifitegrast (100 mg, 63%).

Example 3: Preparation of the Compound of Formula IV

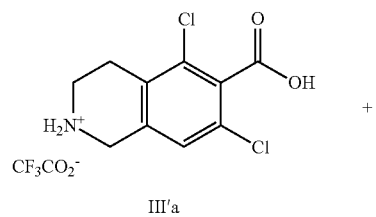

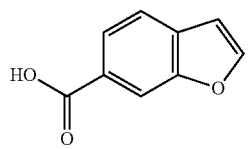

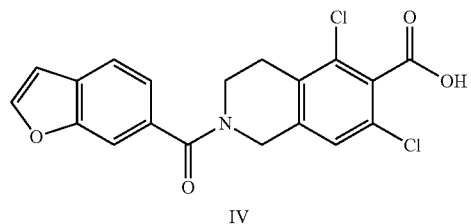

IV

The compound of Formula II (200 mg, 1.23 mmol, 1.0 equiv), HATU (516 mg, 1.36 mmol, 1.1 equiv), DIPEA (967 µL, 5.55 mmol, 4.5 equiv) and THF (2 mL, 10 vol) is charged to a two-neck round bottom flask under nitrogen atmosphere. The reaction mixture was stirred at 20 to 30° C. for 2 hrs. The reaction mixture was slowly added III'a (606 mg, 1.68 mmol, 1.4 equiv) at 20 to 30° C. When the reaction was complete as determined by HPLC analysis, the solvent was evaporated and the mixture was purified by column chromatography, eluting with MeOH/EtOAc=10/90, to give the compound of Formula IV (471 mg, 98%) as white solid.

Example 4: Preparation of Lifitegrast

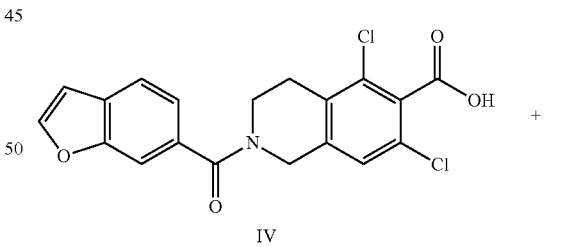

IV

V

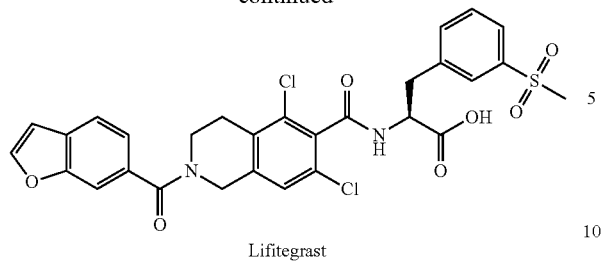

Lifitegrast

The compound of Formula IV (200 mg, 0.51 mmol, 1.0 equiv), HATU (205 mg, 0.54 mmol, 1.05 equiv), DIPEA (400 μL, 2.30 mmol, 4.5 equiv) and THF (2 mL, 10 vol) is charged to a two-neck round bottom flask under nitrogen atmosphere. The reaction mixture was heated to NMT 40° C. for 2 hrs. The resulting solution reaction was cooled to 20 to 30° C. The reaction mixture was slowly added the compound of Formula V (300 mg, 1.23 mmol, 2.4 equiv) at 20 to 30° C. When the reaction was complete as determined by HPLC analysis, the reaction was quenched by addition of 1N HCl. The mixture was extracted with EtOAc and concentrated under reduced pressure to give the oil. The mixture was purified by column chromatography using AcOH/EtOAc=3/97, to give lifitegrast (293 mg, 92%) as white solid.

Example 5: Preparation of the Compound of Formula IV

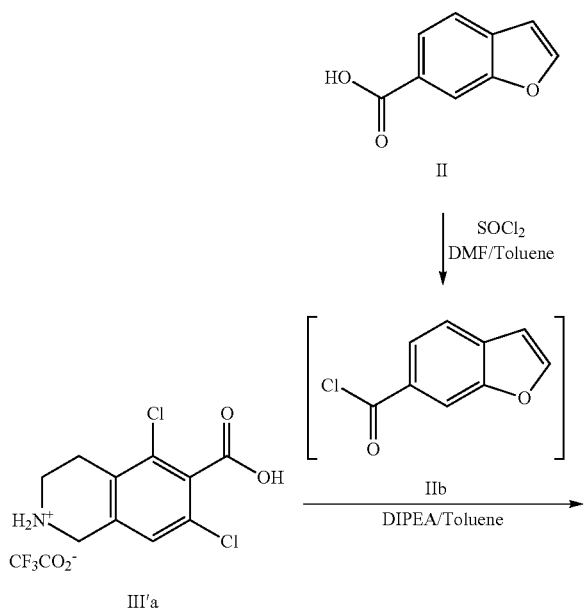

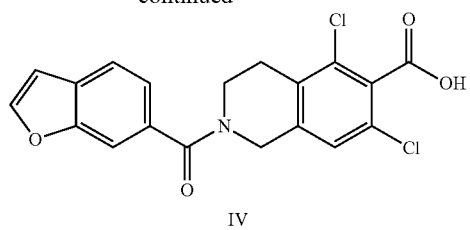

IV

Benzofuran carboxylic acid (II) (6.8 g, 41.94 mmol, 1.0 equiv), DMF (0.01 eq) and Toluene (40.8 mL, 6 vol) is charged to a two-neck round bottom flask under nitrogen atmosphere. Thionyl chloride (6.1 mL, 83.88 mmol, 2.0 equiv) is slowly added while keeping the temperature between 20 to 30° C. The resulting solution was heated to 50° C. and stirred at 50° C. for over 2 hr. When the reaction was complete as determined by HPLC analysis, the solvent was removed under reduced pressure and the acid chloride of compound of Formula II (Formula IIb) was stored under nitrogen.

Compound of Formula III'a (15.91 g, 44.04 mmol, 1.05 equiv) and Toluene (68.0 mL, 10 vol) were added to a two-neck round bottom flask equipped with a thermal couple and a magnetic stirrer. To the mixture was added diisopropylamine (DIPEA) (22.0 mL, 125.82 mmol, 3.0 equiv) at NMT 30° C. The reaction mixture was cooled to 5 to 15° C. and a solution of compound of Formula IIb in Toluene (68.0 mL, 10 vol) was slowly added while keeping the temperature between 5 to 15° C. The reaction mixture was gradually warmed to 20-30° C. and until the reaction was complete. When the reaction was complete as determined by HPLC analysis, the reaction mixture was filtered. The wet cake and DMAc (68.0 mL, 20 vol) was charged to a two-neck round bottom flask equipped with a thermal couple and a magnetic stirrer. The resulting solution was heated to 60° C. and 1N HCl (136.0 mL, 10 vol) was slowly added following with PPW (partially purified water, 204.0 mL, 30 vol) while keeping the temperature at 60° C. After addition was complete the reaction mixture was cooled to 20 to 30° C. and stirred for NLT 2 hr at 20 to 30° C. The solid was filtered and the wet cake was washed with PPW (102.0 mL, 15 vol). The wet cake was dried below 60° C. under vacuum and nitrogen to afford compound of Formula IV (14.5 g, 88%).

Example 6: Preparation of Lifitegrast

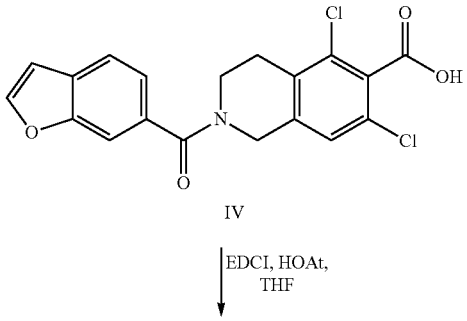

-continued

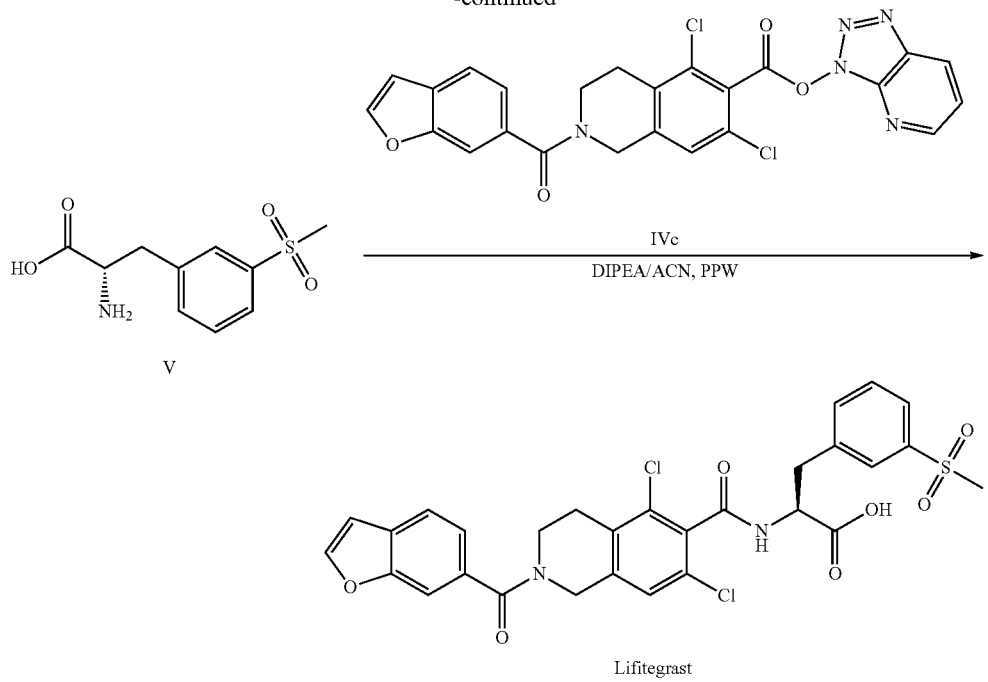

Lifitegrast

The compound of Formula IV (2.0 g, 5.13 mmol, 1.0 equiv), THF (10 mL, 10 vol), HOAt (0.77 g, 5.66 mmol, 1.1 equiv) and EDCI (1.5 g, 7.69 mmol, 1.5 equiv) were charged to a two-neck round bottom flask under nitrogen atmosphere. The resulting solution was heated to 40 to 45° C. and stirred at 40 to 45° C. for over 2 hr. When the reaction was complete as determined by HPLC analysis, the solution was cooled to 20 to 30° C. and PPW (5 mL, 5 vol) was added and stirred at 20 to 30° C. for 30 mins. The solid was filtered and the wet cake was washed with THF/PPW=1/1 (12 mL, 6 vol). The wet cake was dried below 60° C. under vacuum and nitrogen to afford compound of Formula IVc (2.4 g, 91%). The compound of Formula V (718 mg, 2.95 mmol, 1.5 equiv), DIPEA (1.0 mL, 5.91 mmol, 3.0 equiv), PPW (7.5 mL, 7.5 vol), and ACN (7.5 mL, 7.5 vol) were added into a two-necked round bottom flask equipped with a magnetic stirrer and a thermometer under nitrogen at NMT 30° C. The resulting solution was heated to 40 to 45° C. and the compound of Formula IVc (1.0 g, 1.97 mmol, 1.0 equiv) was charged at 40 to 45° C. then stirred at 40 to 45° C. When the reaction was complete as determined by HPLC analysis, the reaction was cooled to 20 to 30° C. The ACN was removed under reduced pressure then PPW (15 mL, 15 vol) and MeOH (7.5 mL, 7.5 vol) was charged to the solution. The resulting solution was cooled to 0 to 5° C. and adjusted with 3N HCl to pH 5.0±0.1 then stirred at 0 to 5° C. for 1 hr. The solid was filtered and the wet cake was washed with ice water (2.4 mL, 6 vol). The resulting crude lifitegrast, PPW (22.5 mL, 22.5 vol) and DIPEA (1.0 mL, 5.91 mmol, 3.0 equiv) were charged to a two-neck round bottom flask following with MeOH (7.5 mL, 7.5 vol). The resulting solution was cooled to 0 to 5° C. and adjusted with 3N HCl to pH 5.0±0.1 then stirred at 0 to 5° C. for 1 hr. The solid was filtered and the wet cake was washed with ice water (2.4 mL, 6 vol). The wet cake was dried below 60° C. under vacuum and nitrogen to afford lifitegrast (1.1 g, 87%).

What is claimed is:

1. A process for preparing the compound of Formula I:

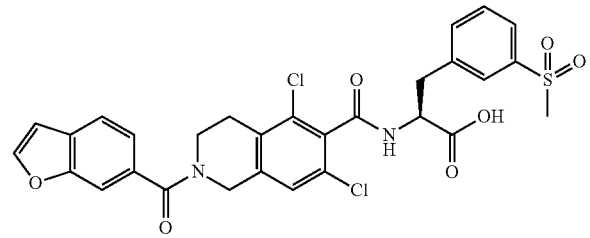

or a pharmaceutically acceptable salt thereof; the process comprising:

a) contacting the compound of Formula II

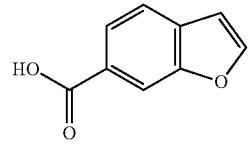

with a first activating reagent in a first activating solvent to provide an activated intermediate of Formula IIa

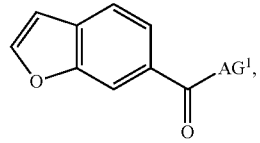

and contacting the activated intermediate of Formula IIa with a compound of Formula III or III'

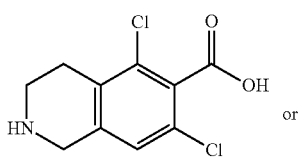
(III)

or

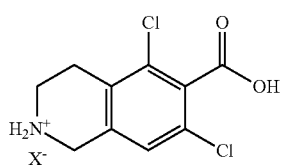
(III')

in a first coupling solvent to provide a compound of Formula IV

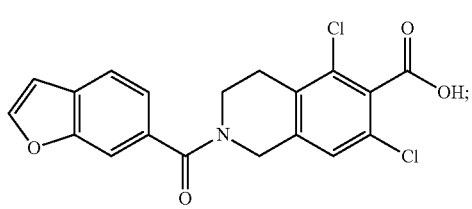
(IV)

and b) contacting the compound of Formula IV with a second activating reagent in a second activating solvent to provide an activated intermediate of Formula IVa

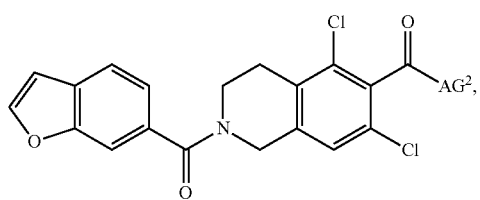
(IVa)

and contacting the activated intermediate of Formula IVa with a compound of Formula V or V'

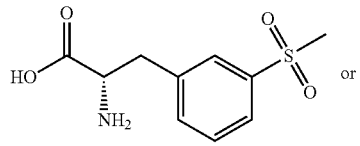
(V)

or

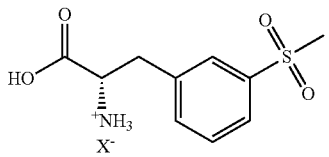
(V')

in a second coupling solvent to provide a compound of Formula I;

wherein $AG^1$ and $AG^2$ are each independently Cl or an activated hydroxyl moiety and $X^-$ is $Cl^-$ $Br^-$, $I^-$ or $CF_3C(O)O^-$.

2. The process according to claim 1, wherein the first activating solvent and the first coupling solvent are each a first solvent; and the second activating solvent and the second coupling solvent are each a second solvent, the first solvent and the second solvent are each independently selected from the group consisting of $C_{1-4}$ alkyl-alcohol, dioxane, N-methyl-2-pyrrolidone (NMP), dimethylacetamide (DMAc), N,N-dimethylmethanamide (DMF), ethyl acetate, acetonitrile, tetrahydrofuran (THF), dimethyl sulfoxide (DMSO), dichloromethane, toluene, water, and mixtures thereof.

3. The process according to claim 2, wherein the first solvent and the second solvent each comprises THF.

4. The process according to claim 1, wherein the first activating solvent, the first coupling solvent, the second activating solvent, and the second coupling solvent are each independently selected from the group consisting of $C_{1-4}$ alkyl-alcohol, dioxane, N-methyl-2-pyrrolidone (NMP), dimethylacetamide (DMAc), N,N-dimethylmethanamide (DMF), ethyl acetate, acetonitrile, tetrahydrofuran (THF), dimethyl sulfoxide (DMSO), dichloromethane, toluene, water, and mixtures thereof.

5. The process according to claim 1, wherein the conversion of step a) and/or step b) further comprise a non-nucleophilic base selected from the group consisting of triethylamine, N,N-diisopropylethylamine (DIPEA), and N-methylmorpholine.

6. The process according to claim 5, wherein the non-nucleophilic base is N,N-diisopropylethylamine (DIPEA).

7. The process according to claim 1, wherein the first activating reagent is a first chlorinating reagent; and the second activating reagent is a second chlorinating reagent, the first chlorinating reagent and the second chlorinating reagent are each independently selected from the group consisting of $(COCl)_2$ (oxalyl chloride), $SOCl_2$ (thionyl chloride), $POCl_3$ (Phosphoryl chloride), and $PCl_5$ (phosphorus pentachloride).

8. The process according to claim 7, wherein the first chlorinating reagent and the second chlorinating reagent are each independently $(COCl)_2$ (oxalyl chloride) or $(SOCl)_2$ (thionyl chloride).

9. The process according to claim 1, wherein the first activating reagent and the second activating reagent are each independently selected from the group consisting of dicyclohexylcarbodiimide (DCC), diisopropylcarbodiimide (DIC), 1-ethyl-3-(3-dimethylaminopropyl)carbodiimide (EDCI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), hydroxybenzotriazole (HOBt), 1-hydroxy-7-azabenzotriazole (HOAt), and mixtures thereof.

10. The process according to claim 9, wherein the first activating reagent and the second activating reagent are each independently O-(7-azabenzotriazol-1-yl)-N,N,N',N'-tetramethyluronium hexafluorophosphate (HATU) or 1-hydroxy-7-azabenzotriazole (HOAt).

11. The process according to claim 1, wherein the activated hydroxyl moiety is the reaction product of a carboxylic acid with dicyclohexylcarbodiimide (DCC), diisopropylcarbodiimide (DIC), 1-ethyl-3-(3-dimethylaminopropyl)carbodiimide (EDCI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), hydroxybenzotriazole (HOBt), 1-hydroxy-7-azabenzotriazole (HOAt), or mixtures thereof.

12. A process for preparing the compound of Formula I:

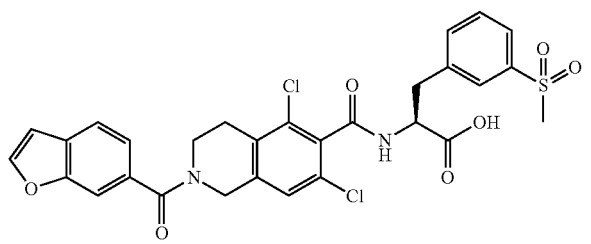

(I)

or a pharmaceutically acceptable salt thereof; the process comprising:

contacting the compound of Formula IV

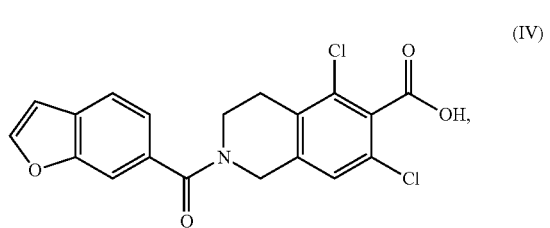 [SMILES: O=C(O)c1c(Cl)cc2c(c1Cl)CCN(C(=O)c1ccc3ccoc3c1)C2]

(IV)

with a activating reagent in an activating solvent to provide an activated intermediate of Formula IVa

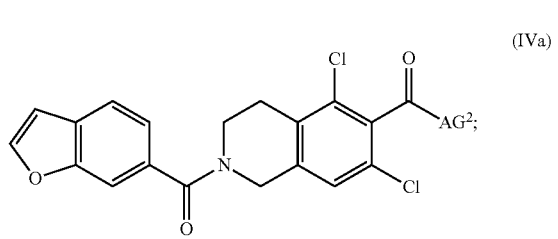

(IVa)

and contacting the activated intermediate of Formula IVa with a compound of Formula V or V'

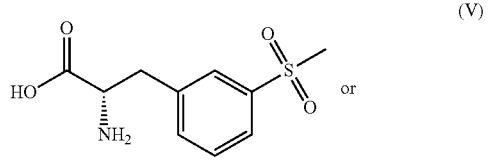

(V)

or

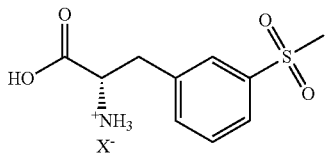

(V')

in a coupling solvent to provide a compound of Formula I, wherein $AG^2$ is Cl or an activated hydroxyl moiety and $X^-$ is $Cl^-$, $Br^-$, $I^-$, or $CF_3C(O)O^-$.

13. The process according to claim 12, wherein the activating solvent and the coupling solvent are each a solvent selected from the group consisting of $C_{1-4}$ alkyl-alcohol, dioxane, N-methyl-2-pyrrolidone (NMP), dimethylacetamide (DMAc), N,N-dimethylmethanamide (DMF), ethyl acetate, acetonitrile, tetrahydrofuran (THF), dimethyl sulfoxide (DMSO), dichloromethane, toluene, water, and mixtures thereof.

14. The process according to claim 12, wherein the activating solvent and the coupling solvent are each independently selected from the group consisting of $C_{1-4}$alkyl-alcohol, dioxane, N-methyl-2-pyrrolidone (NMP), dimethylacetamide (DMAc), N,N-dimethylmethanamide (DMF), ethyl acetate, acetonitrile, tetrahydrofuran (THF), dimethyl sulfoxide (DMSO), dichloromethane, toluene, water, and mixtures thereof.

15. The process according to claim 12, further comprising a non-nucleophilic base selected from the group consisting of triethylamine, N,N-diisopropylethylamine (DIPEA), and N-methylmorpholine.

16. The process according to claim 15, wherein the non-nucleophilic base is N,N-diisopropylethylamine (DIPEA).

17. The process according to any one of claims 12 to 16, wherein the activating reagent is a chlorinating reagent selected from the group consisting of $(COCl)_2$ (oxalyl chloride), $SOCl_2$ (thionyl chloride), $POCl_3$ (Phosphoryl chloride), and $PCl_5$ (phosphorus pentachloride).

18. The process according to claim 17, wherein the chlorinating reagent is $(COCl)_2$ (oxalyl chloride) or $(SOCl)_2$ (thionyl chloride).

19. The process according to claim 12, wherein the activating reagent is selected from the group consisting of dicyclohexylcarbodiimide (DCC), diisopropylcarbodiimide (DIC), 1-ethyl-3-(3-dimethylaminopropyl)carbodiimide (EDCI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), hydroxybenzotriazole (HOBt), 1-hydroxy-7-azabenzotriazole (HOAt), and mixtures thereof.

20. The process according to claim 19, wherein the activating reagent is O-(7-azabenzotriazol-1-yl)-N,N,N',N'-tetramethyluronium hexafluorophosphate (HATU).

21. The process according to claim 12, wherein the activated hydroxyl moiety is the reaction product of a carboxylic acid with dicyclohexylcarbodiimide (DCC), diisopropylcarbodiimide (DIC), 1-ethyl-3-(3-dimethylaminopropyl)carbodiimide (EDCI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), hydroxybenzotriazole (HOBt), 1-hydroxy-7-azabenzotriazole (HOAt), or mixtures thereof.

* * * * *